US008742331B2

(12) United States Patent
Armstrong

(10) Patent No.: US 8,742,331 B2
(45) Date of Patent: Jun. 3, 2014

(54) IMIDAZOLIUM-BASED LIQUID SALTS AND METHODS OF USE THEREOF

(75) Inventor: Daniel W. Armstrong, Arlington, TX (US)

(73) Assignee: Sigma-Aldrich, Co., Saint Louis, MO (US)

( * ) Notice: Subject to any disclaimer, the term of this patent is extended or adjusted under 35 U.S.C. 154(b) by 737 days.

(21) Appl. No.: 12/867,142

(22) PCT Filed: Feb. 17, 2009

(86) PCT No.: PCT/US2009/034290
§ 371 (c)(1), (2), (4) Date: Oct. 12, 2010

(87) PCT Pub. No.: WO2009/103062
PCT Pub. Date: Aug. 20, 2009

(65) Prior Publication Data

US 2011/0036975 A1 Feb. 17, 2011

Related U.S. Application Data

(60) Provisional application No. 61/029,103, filed on Feb. 15, 2008.

(51) Int. Cl.
*B01D 59/44* (2006.01)
*C07D 403/06* (2006.01)

(52) U.S. Cl.
USPC ..................... 250/282; 548/313.7; 548/314.7; 73/23.35; 73/61.52

(58) Field of Classification Search
USPC ....................................................... 548/313.7
See application file for complete search history.

(56) References Cited

U.S. PATENT DOCUMENTS

| | | | | |
|---|---|---|---|---|
| 6,531,241 | B1 | 3/2003 | McEwen | 429/46 |
| 7,931,824 | B2 * | 4/2011 | Gin et al. | 252/299.01 |
| 8,168,801 | B2 * | 5/2012 | Chan et al. | 548/313.7 |
| 8,168,830 | B2 * | 5/2012 | Armstrong et al. | 564/463 |
| 2006/0025598 | A1 * | 2/2006 | Armstrong et al. | 548/101 |
| 2008/0027231 | A1 * | 1/2008 | Armstrong et al. | 548/313.7 |
| 2008/0210858 | A1 * | 9/2008 | Armstrong et al. | 250/282 |
| 2010/0093975 | A1 * | 4/2010 | Chan et al. | 530/328 |
| 2012/0083603 | A1 * | 4/2012 | Armstrong et al. | 540/567 |
| 2012/0215005 | A1 * | 8/2012 | Armstrong et al. | 548/110 |

FOREIGN PATENT DOCUMENTS

| | | | |
|---|---|---|---|
| DE | 33 33 124 | 9/1983 | C01B 33/26 |
| JP | 61-226658 | 10/1986 | G01N 30/74 |
| JP | 2008-503725 | 2/2008 | G01N 30/46 |
| WO | WO 2006/007429 | 1/2006 | A61K 37/00 |

OTHER PUBLICATIONS

Anderson, et al. (2005) "Structure and properties of high stability geminal dicationic ionic liquids." *J. Am. Chem. Soc.*, 127:593-604.
Han, et al. (2005) "Using germinal dicationic ionic liquids as solvents for high-temperature organic reactions." *Org. Lett.*, 7(19):4205-4208.
Han, et al. (2007) "Ionic liquids in separations." *Acc. Chem. Res.* 40(11):1079-1086.
Martinelango, et al. (2005) "Gas-phase ion association provides increased selectivity and sensitivity for measuring perchlorate by mass spectrometry." *Anal.Chem.* 77:4829-4835.
Payagala, et al. (2007) "Unsymmetrical dicationic ionic liquids: manipulation of physicochemical properties using specific structural architectures." *Chem. Mater.* 19:5848-5850.
Remsburg J W, et al. (2007) "Evaluation of dicationic reagents for their use in detection of anions using positive ion mode esi-ms via gas phase ion association." *J. Am. Soc. Mass. Spectrom*, 19(2):261-269.
Rothstein, et al. (1953) "The reactions of organic derivatives of elements capable of valency-shell expansion. Part II. Unsaturated quaternary phosphonium salts." Published on Jan. 1, 1953 on http://pubs.rsc.org I doi:10.1039/JR9530003994.
International Search Report (ISR) and Written Opinion (WO) in PCT/US2009/034293, dated Apr. 15, 2009.
International Search Report (ISR) and Written Opinion (WO) in PCT/US2009/034290, dated Apr. 21, 2009.
Office Action dated Jan. 7, 2013, in European Application No. 09 711 475.5-2404.
Office Action dated Jan. 3, 2013, in European Application No. 09 709 894.1-2404.
Office Action dated Dec. 19, 2012, in Japanese Application No. 2010-546955.
Office Action dated Dec. 19, 2012, in Japanese Application No. 2010-546954.
Office Action dated Mar. 20, 2012, in U.S. Appl. No. 12/867,139.
Office Action dated Apr. 30, 2012, in U.S. Appl. No. 12/867,139.
Office Action dated Jul. 20, 2012, in U.S. Appl. No. 12/867,139.

* cited by examiner

*Primary Examiner* — Kamal Saeed
(74) *Attorney, Agent, or Firm* — Harness, Dickey & Pierce, P.L.C.

(57) ABSTRACT

Imidazolium-based dicationic liquid salts and methods of using such imidazolium-based dicationic liquid salts in techniques such as ESI-MS are provided.

28 Claims, 3 Drawing Sheets

IMIDAZOLIUM-BASED LIQUID SALTS AND METHODS OF USE THEREOF

CROSS-REFERENCED APPLICATIONS

This application claims priority to U.S. provisional application Ser. No. 61/029,103 filed on 15 Feb. 2008. This application contains subject matter that is related to U.S. provisional patent application Ser. No. 61/029,075, co-filed on 15 Feb. 2008. The disclosure of each of the applications identified in this paragraph is incorporated herein by reference in its entirety.

FIELD OF THE INVENTION

The present invention relates to imidazolium-based dicationic liquids salts and their use in various techniques such as electrospray ionization-mass spectrometry (ESI-MS).

BACKGROUND OF THE INVENTION

Room temperature geminal dicationic liquids (or liquid salts) have been shown to possess superior physical properties in terms of thermal stability and volatility compared to traditional ionic liquids. Dicationic liquid salts have been proposed for use as solvents and stationary phases, for example, in gas or liquid chromatography.

U.S. Publication No. 2006/0025598 reports high stability diionic liquid salts and use thereof as stationary phases in gas chromatography.

Anderson J., et al. *J. Am. Chem. Soc.* 2005. 127:593-604 reports the structure and properties of high stability geminal dicationic ionic liquids.

Han X, et al. *Org. Lett.* 2005. 7(19):4205-4208 reports geminal dicationic ionic liquids as solvents for high-temperature organic reactions.

U.S. Pat. No. 6,531,241 to McEwan reports cyclic delocalized cations connected by spacer groups.

Detection and quantitation of anions is of great importance in a wide variety of scientific fields. The advent of electrospray ionization allowed routine analysis of ionic components in a liquid sample. By coupling ESI-MS with a separation method, such as liquid chromatography, a means to separate and detect most compounds can be accomplished. However, problems exist with ESI-MS, such as background peaks, reduced stability of the ion current, undesirable arcing and necessity of using unconventional solvents. Therefore a need exists for new compounds and methods of reducing such problems.

SUMMARY OF THE INVENTION

There is now provided a method of detecting at least one anion by ESI-MS, the method comprising using at least one dicationic liquid salt comprising a dicationic species corresponding in structure to Formula I:

Formula I

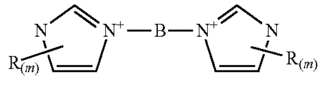

and at least one counter-anion;

wherein:

R is one or more substituents independently selected from the group consisting of alkyl, alkenyl, hydroxyl, alkoxy, carbocyclyl, carbocyclylalkyl, heterocyclyl, heterocyclylalkyl and hydroxyalkyl;

m is zero, 1, 2, 3 or 4;

B is a divalent fragment composed of a chain of one or more moieties selected from the group consisting of $C_1$-$C_{20}$-alkylene, $C_2$-$C_{20}$-alkenylene, $C_2$-$C_{20}$-alkynylene, $(—CH_2\text{-carbocyclyl-}CH_2—)_n$, $(—CH_2\text{-carbocyclyl-})_n$ and polysiloxyl;

wherein $C_1$-$C_{20}$-alkylene, $C_2$-$C_{20}$-alkenylene, and $C_2$-$C_{20}$-alkynylene optionally contain in the chain one or more heteroatoms selected from the group consisting of O, N, S and Si;

wherein B is optionally substituted with one or more substituents selected from the group consisting of alkyl, alkenyl, alkynyl, alkoxy and halo;

n is selected from the group consisting of 1 to 20, inclusive.

Other embodiments, including particular aspects of the embodiments summarized above will be evident from the detailed description that follows.

DETAILED DESCRIPTION OF THE INVENTION

Figure 1:
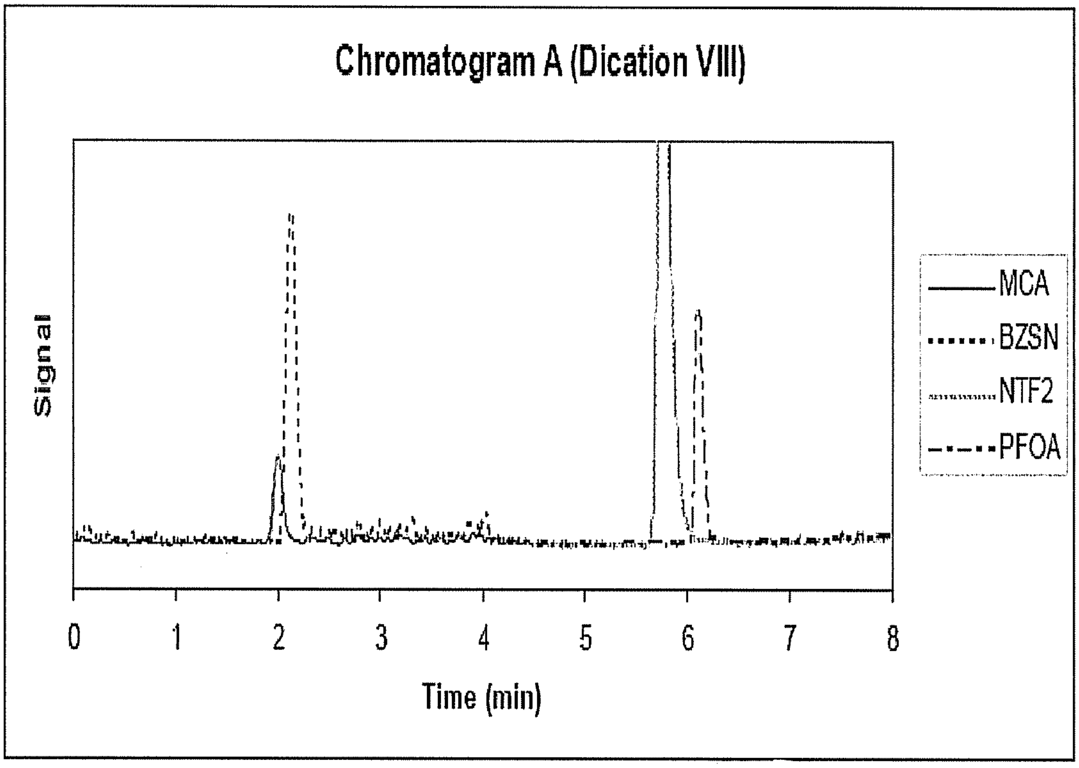
FIG. 1 is a chromatogram showing the separation of a sample containing four anions using dicationic species VIII. The masses monitored are the sum of the mass of each anion and the mass of the corresponding dicationic salt (reagent).
Figure 2:
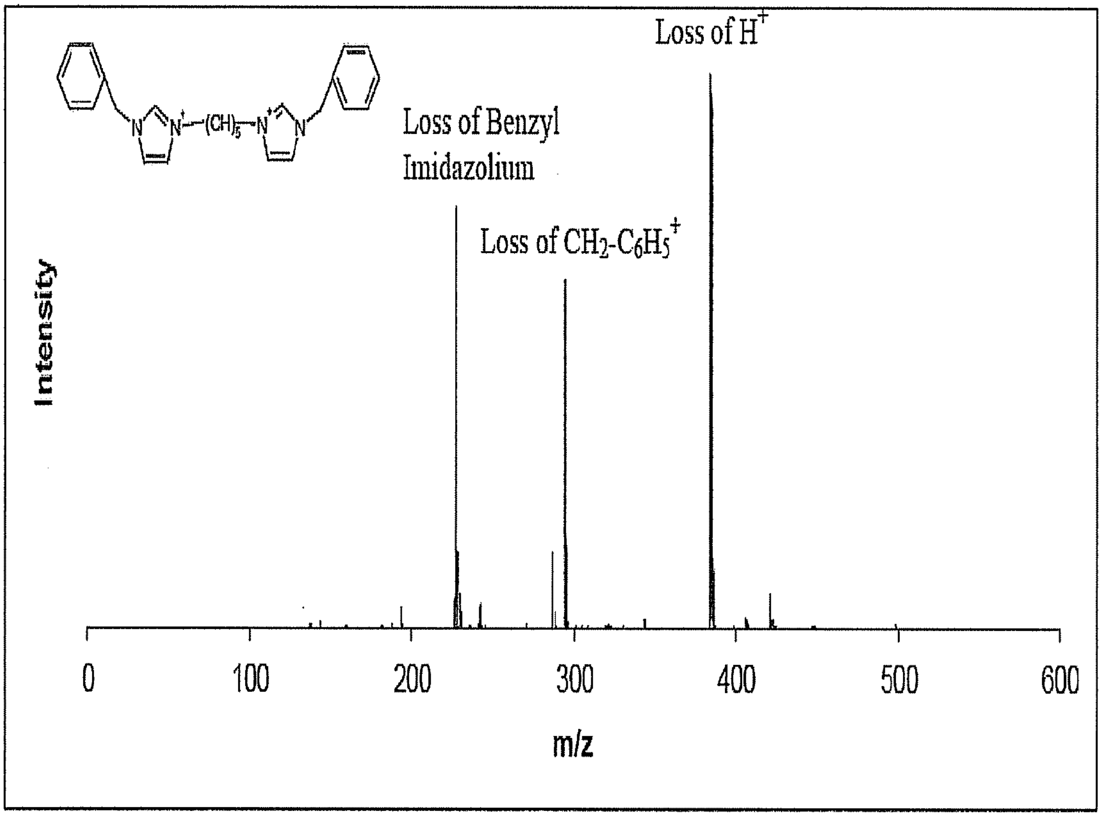
FIG. 2 is a mass spectrum of the mobile phase containing dicationic reagent XIV under typical operating settings for chromatography. The three most pertinent peaks are fragments of dicationic reagent XIV. These fragments can be monitored after excitation of a dication-anion complex to typically lower detection limits.
Figure 3:
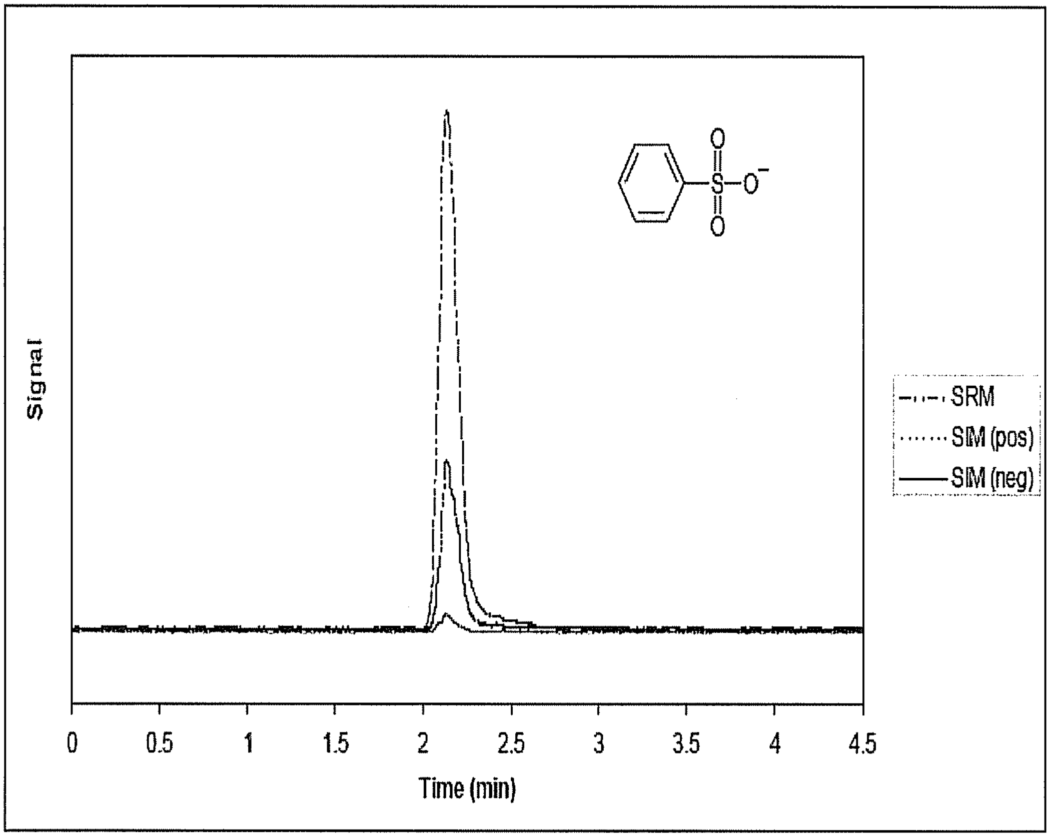
FIG. 3 is an overlapping chromotagram of three separate injections of a 100 ng/mL sample of benzene sulfonate. The solid line represents the use of negative mode, monitoring the mass of the anion (methanol being added post column). When 40 μM of dication XIV in methanol is added post column, the mass of the dication-anion complex can be monitored and gives a significant increase in S/N (dotted line). When single reaction monitoring is used, an even further increase in S/N can be seen, as shown by the alternating line.

In various aspects of the invention, dicationic liquid salts are provided and methods of using such dicationic liquid salts, for example, to detect an anion by ESI-MS.

U.S. Publication No. 2008/0027231 is a continuation-in-part of U.S. Publication No. 2006/0025598. U.S. Publication No. 2008/0027231 reports both symmetric and unsymmetric dicationic liquid salts. U.S. Publication No. 2008/0027231 also reports the use of unsymmetric dicationic liquid salts in various separation techniques including ESI-MS. All of the foregoing are incorporated by reference in their entirety.

A. DEFINITIONS

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl.

A carbocyclyl may alternatively be polycyclic or contain more than one ring. Examples of polycyclic carbocyclyls include bridged, fused, spirocyclic, and isolated carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicycle[2.2.1]hept-2-enyl, and adamantanyl. In a fused-ring carbocyclyl system, multiple rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl. In an isolated carbocyclyl, the rings are separate and independent, as they do not share any common atoms, but a linker bond exists between the rings.

The term "carbocyclyl" also encompasses protonated carbocyclyls, such as

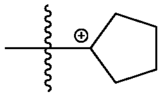

and

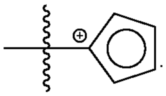

.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., N, P, As, O, S and Si), with the remaining ring atoms being independently selected from the group consisting of carbon, oxygen, nitrogen, and sulfur. A heterocyclyl may be a single-ring (monocyclic) or polycyclic ring structure.

The term heterocyclyl encompasses protonated heterocyclyls such as pyridinium, pyridazinium, pyrimidinium, pyrazinium, imidazolium, pyrazolium, thazolium, oxazolium and triazolium.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic or contain more than one ring. Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, multiple rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

As used herein, the term "alkyl" (alone or in combination with another term(s)) refers to an alkane-derived radical containing from 1 to 20, carbon atoms. Alkyl includes straight chain alkyl and branched alkyl. Straight chain or branched alkyl groups contain from 1-15 carbon atoms, such as methyl, ethyl, propyl, isopropyl, butyl, t-butyl, and the like. Alkyl can be further modified with one or more cycloalkyls. For example, alkyl may contain or be interrupted by one or more cycloalkyl portions. The alkyl group is attached at any available point to produce a stable compound.

The term "alkylene" (alone or in combination with another term(s)) refers to a divalent alkane-derived radical containing 1-20, preferably 1-15, carbon atoms, from which two hydrogen atoms are taken from the same carbon atom or from different carbon atoms. Examples of alkylene include, but are not limited to:

methylene ($-CH_2-$), ethylene ($-CH_2CH_2-$), propylene ($-CH_2CH_2CH_2-$), butylene ($-CH_2CH_2CH_2CH_2-$), pentylene ($-CH_2CH_2CH_2CH_2CH_2-$), hexylene ($-CH_2CH_2CH_2CH_2CH_2CH_2-$), heptylene ($-CH_2CH_2CH_2CH_2CH_2CH_2CH_2-$), octylene ($-CH_2CH_2CH_2CH_2CH_2CH_2CH_2CH_2-$), nonylene ($-CH_2CH_2CH_2CH_2CH_2CH_2CH_2CH_2CH_2-$), decylene ($-CH_2CH_2CH_2CH_2CH_2CH_2CH_2CH_2CH_2CH_2-$), undecylene ($-CH_2CH_2CH_2CH_2CH_2CH_2CH_2CH_2CH_2CH_2CH_2-$), dodecylene ($-CH_2CH_2CH_2CH_2CH_2CH_2CH_2CH_2CH_2CH_2CH_2CH_2-$), and the like.

The term "polysiloxyl" (alone or in combination with another term(s)) refers to a divalent radical composed of oxygen and silicon containing 1-20 atoms. Examples include a $(—Si—O—Si—)_a$ or $(—Si—O—)_n$ backbone chain wherein n is from 1-20. Polysiloxyl also encompasses when the backbone chain is substituted with one or more oxygen atoms.

The term "polyether" (alone or in combination with another term(s)) refers to a divalent radical composed of more than one ether group containing 1-20 atoms. Polyethylene glycol is an example of a parent compound which provides a polyether divalent radical. Another class of polyethers is a linear alkoxy divalent radical.

The term "alkoxy" (alone or in combination with another term(s)) means an alkylether, i.e., —O-alkyl. Examples of such a substituent include methoxy ($—O—CH_3$), ethoxy, n-propoxy, isopropoxy, n-butoxy, iso-butoxy, sec-butoxy, tert-butoxy, and the like.

The term "diionic salt" is used to describe a salt molecule, although, as the context suggests, it may be used synonymously with "diionic liquid" ("DIL") and "diionic liquid salt" ("DILS"). A "diionic liquid" or "diionic liquid salt" in accordance with the present invention is a liquid comprised of diionic salts. Thus, sufficient DS molecules are present such that they exist in liquid form at the temperatures indicated herein. This presumes that a single DS molecule is not a liquid. A diionic liquid is either (1) a dicationic liquid or (2) a dianionic liquid.

A "dicationic liquid salt" or "dicationic liquid", as mentioned above, is either a salt molecule or a liquid comprised of dicationic salt(s), wherein the dicationic salt(s) is formed between a dicationic species and one or more counter-anions of equal and opposite charge. The term is not meant to embrace a single species that has a +2 or −2 charge such as $Mg^{+2}$ or $SO_4^{-2}$. Rather it contemplates a single molecule with two discreet monocationic groups, usually separated by a bridging group. The dicationic liquid of the present invention can also be a mixture of one or more dicationic liquid salts as defined herein.

In general, there may be different types of monocationic groups to yield an "unsymmetric" dicationic species or the dicationic liquid salt may be "geminal" which means both monocationic groups are not only the same charge, but also the same structure. The species contemplated herein are "geminal" or "symmetric" dicationic species.

B. DICATIONIC LIQUID SALTS

In one embodiment, a dicationic liquid salt is provided. The dicationic liquid salt comprises a dicationic species corresponding in structure to Formula I:

Formula I

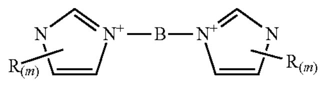

and at least one counter-anion;

The variable R is one or more independently selected substituents such as alkyl, alkoxy, carbocyclyl, carbocyclylalkyl, heterocyclyl, heterocyclylalkyl and hydroxyalkyl.

In a particular aspect, R is one or more independently selected substituents such as methyl, ethyl, propyl, butyl, ethenyl, methoxy, ethoxy, propoxy, butoxy, phenyl, cyclohexane, benzyl, cyclohexanemethyl, hydroxymethyl, hydroxyethyl and hydroxypropyl.

The variable m is zero, 1, 2, 3 or 4; particularly zero, 1 or 2; and more particularly 1 or 2.

The variable B is a divalent fragment (or "bridge") composed of a chain of one or more moieties such as $C_1$-$C_{20}$-alkylene, $C_2$-$C_{20}$-alkenylene, $C_2$-$C_{20}$-alkynylene, $(—CH_2\text{-carbocyclyl-}CH_2—)_n$, and ($—CH_2$-carbocyclyl-), where n is 1 to 20, inclusive, and polysiloxyl.

In a particular aspect, $C_1$-$C_{20}$-alkylene, $C_2$-$C_{20}$-alkenylene, and $C_2$-$C_{20}$-alkynylene may optionally contain in the chain one or more heteroatoms such as O, N, S and Si.

In one aspect, B is $C_1$-$C_{20}$-alkylene containing one oxygen atom (such as an ether); and in another aspect B is $C_1$-$C_{20}$-alkylene containing more than one oxygen atom (such as a polyether).

In a particular aspect B is a divalent radical such as methylene, ethylene, propylene, butylene, pentylene, hexylene, heptylene, octylene, nonylene, decylene, undecylene or dodecylene.

In another aspect, B is optionally substituted with one or more substituents independently selected from alkyl, alkenyl, alkynyl, alkoxy and halo. In a particular aspect, B is substituted with one or more substituents independently selected from methyl, ethyl, propyl, butyl, methenyl, ethenyl, propenyl, butenyl, methoxy, ethoxy, propoxy, butoxy, F, Br and Cl. In a further particular aspect, B is substituted with F.

In a particular aspect, B is $C_1$-$C_{20}$-alkylene, $C_2$-$C_{20}$-alkenylene, $(—CH_2\text{-carbocyclyl-}CH_2—)_n$ or $(—CH_2\text{-carbocyclyl-})_n$ where n is 1-12 inclusive. And in a further particular aspect, B is $(—CH_2\text{-phenyl-}CH_2—)_n$, $(—CH_2\text{-cyclohexane-}CH_2—)_n$, $(—CH_2\text{-phenyl-})_n$, $(—CH_2\text{-cyclohexane-})_n$; where n is 1-12 inclusive.

In a particular aspect, B is $C_1$-$C_8$-alkylene.

In another particular aspect, when B is $C_3$-alkylene, R is not methyl when m is 1 or 2; and when B is $C_5$-alkylene, R is not methyl when m is 1; and when B is $C_6$-alkylene, R is not methyl when m is 1.

In one embodiment, m is 1, 2, 3 or 4; and B is $C_1$-$C_8$-alkylene, $C_2$-$C_{20}$-alkenylene or $(—CH_2\text{-carbocyclyl-}CH_2—)_n$ or $(—CH_2\text{-carbocyclyl-})_n$.

In another embodiment, m is 1, 2 or 3; B is $C_1$-$C_8$-alkylene, $C_2$-$C_{20}$-alkenylene or $(—CH_2\text{-carbocyclyl-}CH_2—)_n$; and n is 1 to 12, inclusive.

In another embodiment, R is $C_2$-$C_{10}$-alkyl, hydroxyl, carbocyclylalkyl, heterocyclylalkyl or hydroxyalkyl; m is 1 or 2; B is $C_1$-$C_8$-alkylene, $C_2$-$C_{20}$-alkenylene, $(—CH_2\text{-phenyl-}CH_2—)_n$ or $(—CH_2\text{-cyclohexane-}CH_2—)_n$; wherein B is optionally substituted with one or more substituents independently selected from the group consisting of F, Cl, Br, methyl, ethyl, propyl, butyl, methoxy, ethoxy, propoxy and butoxy; wherein B optionally contains in the chain one or more oxygen atoms; and n is 1 to 12, inclusive.

In another embodiment, R is ethyl, propyl, butyl, hydroxyalkyl or benzyl; m is 1; B is $C_1$-$C_8$-alkylene or $(—CH_2\text{-phenyl-}CH_2—)_n$; wherein B is optionally substituted with one or more substituents independently selected from the group consisting of F, Cl and Br; wherein B optionally contains in the chain one or more oxygen atoms; and n is 1.

In another embodiment, m is 1, 2, 3 or 4; and B is $C_1$-$C_{20}$-alkylene, $C_2$-$C_{20}$-alkenylene, $(—CH_2\text{-carbocyclyl-}CH_2—)_n$ or $(—CH_2\text{-carbocyclyl-})_n$.

In another embodiment, m is 1, 2 or 3; B is $C_1$-$C_{20}$-alkylene, $C_2$-$C_{20}$-alkenylene, $(—CH_2\text{-carbocyclyl-}CH_2—)_n$ or $(—CH_2\text{-carbocyclyl-})_n$; and n is 1 to 12, inclusive.

In another embodiment, R is $C_1$-$C_{10}$-alkyl, hydroxyl, carbocyclylalkyl, heterocyclylalkyl, hydroxyalkyl; m is 1 or 2; B is $C_1$-$C_{20}$-alkylene, $C_2$-$C_{20}$-alkenylene, $(—CH_2\text{-phenyl-}CH_2—)_n$ or $(—CH_2\text{-cyclohexane-}CH_2—)_n$, $(—CH_2\text{-phenyl-})_n$ or $(—CH_2\text{-cyclohexane-})_n$; wherein B is optionally substituted with one or more substituents independently selected from the group consisting of F, Cl, Br, methyl, ethyl, propyl, butyl, methoxy, ethoxy, propoxy and butoxy; wherein B optionally contains in the chain one or more oxygen atoms; and n is 1 to 12, inclusive.

In another embodiment, R is methyl, ethyl, propyl, butyl, hydroxyalkyl or benzyl; m is 1; B is $C_1$-$C_8$-alkylene or $(—CH_2\text{-phenyl-}CH_2—)_n$; wherein B is optionally substituted with one or more substituents independently selected from the group consisting of F, Cl and Br; wherein B optionally contains in the chain one or more oxygen atoms; and n is 1.

Examples of dicationic species contemplated by the invention are shown in Table 1 in the Examples section below.

In general, the counter-anion(s) used to create the dicationic liquid salt may be any suitable counter-anion(s). The salt forming counter-anions may be monoionic such as, for example only, $Br^-$, or dianionic, such as, again for example only, succinic acid. The counter-anions need not be identical. Examples of suitable counter-anions include, without limitation, F, $Br^-$, $Cl^-$, dicarboxylate, disulfonate, disulfate, triflate, $NTf_2^-$, $PF_6^-$ and $BF_4^-$ may be used. In a particular aspect, triflate, $NTf_2^-$, haloalkylsulfonate and halocarboxylate is used.

In one embodiment, the dicationic liquid salt has a solid/liquid transformation temperature at about 100° C. or lower, will not substantially decompose and is substantially nonvolatile at a temperature below 200° C. and has a liquid range of about 200° C. or higher. In another embodiment, the present invention comprises a dicationic liquid salt having a temperature of solid/liquid transformation temperature at 25° C. or lower, which will not substantially decompose and is substantially nonvolatile at a temperature below 300° C. or has a liquid range of about 300° C. or higher.

In one embodiment, either the dicationic species is chiral, having at least one stereogenic center. In such instances, the dicationic liquid salts may be racemic (or in the case of diastereomers, each pair of enantiomers is present in equal amounts) or they may be optically enhanced. "Optically enhanced" in the case of enantiomers means that one enantiomer is present in an amount which is greater than the other. In the case of diastereomers, at least one pair of enantiomers is present in a ratio of other than 1:1. Indeed, the dicationic liquid salts may be "substantially optically pure" in which one enantiomer or, if more than one stereogenic center is present, at least one of the pairs of enantiomers, is present in an amount of at least about 90% relative to the other enantiomer. The diionic liquid salts of the invention may also be optically pure, i.e., at least about 98% of one enantiomer relative to the other.

C. USE IN ESI-MS

In a further embodiment, the invention provides a method of detecting a charged molecule using electrospray ionization-mass spectrometry (ESI-MS). The at least one dicationic liquid salt may be used as a reagent to detect charged anions by ESI-MS.

Therefore, in one embodiment, a method of detecting at least one anion is provided. The method comprises using at least one dicationic liquid salt comprising a dicationic species corresponding in structure to Formula I:

Formula I

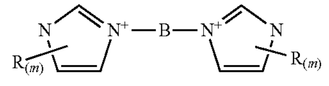

and at least one counter-anion, wherein R, m and B are as described above.

The at least one counter-anion used for ESI-MS is $F^-$ and/or $OH^-$.

In the method, a suitable amount of the dicationic species of the invention having the opposite charges is added to the sample. The dicationic species and the charged molecule form a salt complex. The salt complex is generally a solid. The dicationic species contains at least one more opposite charge than the charged molecule to be detected such that the complex has a net charge. In a particular aspect, the dicationic species contains no more than one opposite charge than the charged molecule to be detected such that the complex has a net charge of +1 or −1. However, +2 or −2 or even higher charge difference can also be used. The complex is then detected using ESI-MS. The formation of the complex converts the charged molecule into an ion having a higher mass to charge ratio, m/z, which can be transferred by ESI more efficiently due to mass discrimination.

In a particular embodiment, ESI-MS is carried out in the positive ion mode.

In another particular embodiment, the dicationic liquid salt pairs with a single anion yielding a positively charged complex.

In another particular embodiment, the dicationic liquid salt is added to a carrier flow solvent for use in ESI-MS. The dicationic liquid salt may be in a solution of about 1 μM to about 200 μM which is added to the carrier flow solvent.

The carrier flow solvent is any suitable water-miscible organic solvent or a mixture of water and the water-miscible organic solvent. Examples of such water-miscible organic solvents include, without limitation, methanol, ethanol, propanol, acetonitrile, tetrahydrofuran and dioxane.

In another embodiment, ESI-MS may be used alone or coupled with a separation method. Examples of such separation techniques include, without limitation, liquid chromatography ("LC"), high performance liquid chromatography ("HPLC"), ion chromatography, ion-exchange chromatography, solid phase extraction ("SPE"), solid phase microextraction ("SPME"), task-specific SPME ("TS-SPME") and SPME/MALDI which are discussed below. In a particular aspect, the dicationic liquid salt is added to the carrier flow solvent following the separation technique.

In another particular embodiment, the method includes selecting a dicationic species that has a desired composition and structure, e.g., a desired charged group structure and a desired mass, or a combination thereof. The charged groups in the dicationic species can be selected based on the composition and structure of the charged molecule to be detected. In a particular aspect, the dicationic species is specific for the charged molecule to be detected. Thus, it is preferable that the charged group of the dicationic species is such that it binds strongly with the charged molecule to be detected. More preferably, the charged groups of the dicationic species is such that it does not bind strongly with other charged molecules, in the sample. Using a dicationic species that is specific for a charged molecule of interest allows high selectivity in detecting the charged molecule.

The mass of the dicationic species can be selected to achieve optimal detection by the mass spectrometer. In general, a dicationic species having a large mass is used. In a particular embodiment, the dicationic species is selected such that the complex has a m/z at least 50. Most commercial single quadruple mass spectrometers are designed to have their optimum performance at m/z values significantly higher than 100. Thus, in another particular embodiment, the dicationic species is selected such that the complex has a m/z significantly higher than 100, e.g., at least about 200, at least about 300, or at least about 400. A person skilled in the art will understand that the mass of the dicationic species depends on the sizes of the charged groups as well as the bridging group. One or more of these can be varied to obtain a dicationic species of desired mass. More preferably, the dicationic species has no more than one opposite charge than the charged molecule to be detected such that the complex has a net charge of +1 or −1, i.e., z=1. The lower the value of z, the higher is m/z, which leads to optimum detection performance.

In a further embodiment, the method includes selecting a dicationic liquid salt that dissociates with high yield. This can be achieved by selecting a dicationic liquid salt containing suitable counterions. In cases where a dicationic liquid salt having desired ionic groups but less desirable counterions, it can be converted to a dicationic liquid salt containing the desired counterions by ion exchange.

In a particular embodiment, a fluoride salt of a dicationic species is used as a reagent for ESI-MS, which, if not available, can be converted from a dihalide, a bromide or an iodide salt by anion exchange.

In another particular embodiment, the invention provides a method of detecting a plurality of different charged molecules by mass spectrometry using a plurality of different dicationic species of the invention. Each of the dicationic species is selected to specifically bind one of the different charged molecules. Preferably, the different dicationic species have different masses such that the complexes formed with their respective charged molecules can be detected separately.

Mass spectrometry can be carried out using standard procedures known in the art.

Benefits of using the dicationic liquid salts as a reagent include, without limitation, (a) moving anions to a higher mass range out of the low mass regions dominated by chemical noise, (b) increasing sensitivity for anions with masses near the low mass cutoff of quadrupole instruments (e.g. traps), and (c) helping to discriminate against interferences between reagent and sample compound having similar mass to charge ratio.

D. SOLVENTS

This invention is also directed to solvents comprising one or more dicationic liquid salts in accordance with the invention.

In some embodiments, the solvent comprises one dicationic liquid salt.

In other embodiments, the solvent comprises more than one dicationic liquid salt.

The “symmetric” dicationic liquid salts of the invention can also be used in combination with any “unsymmetric” diionic species as a mixture. Such mixtures can comprise an unsymmetric dicationic liquid salt and a symmetric dicationic salt of the invention at a ratio such that the mixture has the desired melting temperature and/or desired interactions with other molecules. Thus, in one embodiment, the invention provides a dicationic liquid salt comprising at least one “unsymmetric” dicationic liquid salt and at least one symmetric dicationic liquid salt of the invention at a suitable proportion. A person skilled in the art would be able to determine the proportion of the symmetric and unsymmetric dicationic salts when used as a mixture according to the particular application. In a particular embodiment, in the above described mixture diionic salts are dicationic salts.

The dicationic liquid salts of the present invention can be used in pure or in substantially pure form as carriers or as solvents. “Substantially” in this context means no more than about 10% of undesirable impurities. Such impurities can be other undesired dicationic salts, reaction by-products, contaminants or the like as the context suggests. In an intended mixture of two or more DILSs, neither would be considered an impurity. Because a DILS is non-volatile and stable, a DILS can be recovered and recycled and pose few of the disadvantages of volatile organic solvents. Because of their stability over a wide liquid range, in some instances over 400° C., a DILS can be used in chemical synthesis that requires both heating and cooling. Indeed, these solvents may accommodate all of the multiple reaction steps of certain chemical syntheses. Of course, a DILS may be used in solvent systems with co-solvents and gradient solvents and these solvents can include, without limitation, chiral ionic liquids, chiral non-ionic liquids, volatile organic solvents, non-volatile organic solvents, inorganic solvents, water, oils, etc. It is also possible to prepare solutions, suspensions, emulsions, colloids, gels and dispersions using a DILS. Dicationic liquid salts in accordance with the invention may be used in any mixture, including different dications, different dianions and mixtures of dications and dianions. For example, one or more of the dicationic liquid salts of the invention may be mixed with diionic liquid salts as described in U.S. Patent Publication No. 2006/0025598, the text of which is hereby incorporated by reference.

In another embodiment, one or more dicationic liquid salts can be used as a solvent for dissolution, suspension or dispersion of solids or liquid mixed therewith or as a reaction solvent for chemical reactions. Both are intended by the term solvent. In a particular embodiment, a solvent comprises: one or more dicationic liquid salt as noted above having a solid/liquid transition temperature of about 500° C. or lower, more preferably about 400° C. or lower and having a liquid range of about 200° C. or higher; and, in another embodiment, stability is measured by being substantially non-volatile at a temperature of about 200° C. or below. Both dicationic liquid salts and the solvents made therefrom may be chiral and optically enhanced.

E. STATIONARY PHASES AND POLYMERIZATION

In addition to being useful as solvents and reaction solvents, the dicationic liquid salts of the present invention can be used to perform separations as, for example, the stationary phase for gas-liquid chromatography. In addition to discrete dicationic liquid salts, it is also possible to produce polymers of these materials. Polymers may include the dicationic liquid salts within the backbone or as pendant groups.

Therefore, in another embodiment, there is provided an immobilized dicationic liquid salt including one or more dicationic liquid salts (with or without monoionic materials) as stationary phases, particularly in GC. These stationary phases are highly selective, highly stable, and highly resistant to temperature degradation. These materials can be non-cross-linked (which often means that they are absorbed or adsorbed on a solid support or column), can be “partially” cross-linked or “more highly” cross-linked (which often means that they are “immobilized” on a solid support or column) and can be composed of a mixture of dicationic liquid salts and dicationic material and/or monocationic materials or can be made completely of dicationic liquid salts in accordance with the present invention. The presence of unsaturated groups facilitates cross-linking and/or immobilization.

In the case of non-cross-linked stationary phases, the dicationic liquid salt(s) used may be saturated, unsaturated or a mixture of both. It should be understood, however, particularly if some amount of unsaturated dicationic liquid salt(s) is used, and especially where heat is used to fix the stationary phase, or the stationary phase is heated during use, as in gas chromatography ("GC"), some degree of cross-linking is possible.

"Partially" cross-linked stationary phases in accordance with the present invention permit production of a more stable, highly selective stationary phase, allowing for high efficiency separations at temperatures up to approximately 280° C. In "partially cross-linked" stationary phases, there can be a mixture of mono and diionic species and the amount of diionic liquid salt used will be equal to or less than the amount of monoionic species used.

"More highly" cross-linked stationary phases in accordance with the present invention can provide superior efficiency and stability even at temperatures up to 350° C. and higher. In "more highly cross-linked" stationary phases, the amount of diionic species (diionic liquid salt(s)) will surpass that of any monoionic species. Preferably, more highly cross-linked stationary phases will be composed substantially exclusively (90% or more) of immobilized diionic liquid salt(s) in accordance with the invention. Indeed, they are preferably purely diionic liquid salt(s). In either case, the monoionic species and the diionic species used preferably include unsaturation. The monoionic species will generally have a single multiple bond, the diionic liquid salt(s) will generally have two or more multiple bonds (double bonds/triple bonds). Of course, the diionic species can have but a single unsaturated bond as well. These unsaturated bonds not only allow cross-linking, but also facilitate immobilization. Mixtures of saturated and unsaturated species may also be used, particularly in the case of non-cross-linked stationary phases.

In a particular embodiment, the stationary phases are made from a diionic species which is chiral and optically enhanced. Moreover, cross-linking and/or immobilization of the DILS in a column as a stationary phase, or to a solid support for SPE, SPME, TS-SPME, SPME/MALDI, ion chromatography, ion exchange chromatography, headspace analysis or other analytical or separation technique, does not appear to affect the selectivity of the stationary phase, thereby preserving its dual nature retention behavior.

And while stationary phases for GC and, in particular, capillary GC are one particular aspect of the present invention, the diionic liquid salt(s), either alone or in combination with monoionic liquid salt(s) can be used as a stationary phase in other forms of chromatography including, for example, LC and HPLC. Not only are the methods of creating stationary phases, solid supports and/or columns containing same contemplated, the stationary phases, solid supports and columns themselves and the use of columns and solid supports containing these stationary phases in chromatography, and other analytical or separation techniques are contemplated as specific aspects of the invention.

A DILS can be coated on a capillary (or solid support) and optionally, subsequently polymerized and/or cross-linked by, for example, two general methods. In the first method, the DILS is coated via the static coating method at 40° C. using coating solution concentrations ranging from 0.15-0.45% (w/w) using solutions of methylene chloride, acetone, ethyl acetate, pentane, chloroform, methanol, or mixtures thereof. After coating of the DILS is complete, the column is purged with helium and baked up to 100° C. The efficiency of naphthalene (other molecules such as n-hydrocarbons or Grob Test Mixture can also be used for this purpose) is then evaluated to examine the coating efficiency of the monomer ionic liquid stationary phase. If efficiency is deemed sufficient, the column is then flushed with vapors of azo-tert-butane, a free radical initiator, at room temperature. After flushing with the vapors, the column is then fused at both ends and heated in an oven using a temperature gradient up to 200° C. for 5 hours. The column is gradually cooled and then re-opened at both ends, and purged with helium gas. After purging with helium gas overnight, the column is then heated and conditioned up to 200° C. After conditioning, the column efficiency is then examined using naphthalene at 100° C. and the stationary phase coated layer examined under a microscope. Note that the cross-linking process can, and often does, also cause immobilization. "Immobilized" in the context of the invention means covalently or ionically bound to a support or to another ionic liquid (including diionic liquid salts) or both. This is to be compared with ionic liquids which may be absorbed or adsorbed on a solid support. Solid supports in these particular instances are intended to include columns (e.g., the walls of the columns).

It is not necessary, however, to cross-link these materials prior to their use in GC. They may be adsorbed or absorbed in a column, or indeed on any solid support. However, at higher temperatures, their viscosity may decrease and they can, in some instances, flow and collect as droplets which can change the characteristics of the column. Immobilization or partial cross-linking also reduces the vapor pressure of the stationary phase film which translates into lower column bleed thereby increasing the useful upper temperature limit of the phase and column.

The second method involves adding up to 2% of the dicationic liquid salt monomer weight of 2,2'-azobisisobutyronitrile ("AIBN") free radical initiator to the coating solution of the monomer. The capillary column is then filled with this solution and coated via the static coating method. After coating, the capillary column is then sealed at both ends and placed in an oven and conditioned up to 200° C. for 5 hours. The column is gradually cooled and then re-opened at both ends, and purged with helium gas. After purging with helium gas overnight, the column is then heated and conditioned up to 200° C. After conditioning, the column efficiency is then examined using naphthalene at 100° C. and the stationary phase coated layer examined under a microscope.

In addition to the free radical polymerization of an alkene, other polymerization reactions involve other functional groups either attached to the aromatic ring of the cation or the bridging chain connecting two cations (to form a dication). Examples of such reactions may include cationic and anionic chain growth polymerization reactions, Ziegler-Natta catalytic polymerization, and step-reaction polymerization. The use of two different monomers to form copolymers through addition and block copolymerization can also be achieved. Additionally, condensation polymerization can be used to connect through functional groups such as amines and alcohols. All polymerization and cross-linking reactions discussed in the following two references can be used: "Comprehensive Polymer Science—The Synthesis, Characterization, Reactions and Applications of Polymers" by Sir Geoffrey Allen, FRS; and "Comprehensive Organic Transformations: a guide to functional group preparations"

by Richard C. Larock. 2nd Edition. Wiley-VCH, New York. Copyright, 1999. ISBN: 0471190314.

In another embodiment, there is provided a process which includes the free radical reaction of ionic liquid monomers to provide a more durable and robust stationary phase, as well as the cross-linked and/or immobilized stationary phases and the columns that include same. By partially cross-linking the ionic liquid stationary phase using a small percentage of free radical initiator, high efficiency capillary columns are produced that are able to endure high temperatures with little column bleed. It was found that low to moderate temperature separations (30° C.-280° C.) can be carried out with high selectivity and efficiency using special partially cross-linked ionic liquid stationary phase mixtures. These stationary phases retain their "gelatinous," "semi liquid," amorphous state. For separations conducted at higher temperatures (300° C.-400° C.), more highly cross-linked/immobilized stationary phases are well-suited to provide high selectivity and efficient separations with low column bleed. The effect of different functionalized ionic liquid salt mixtures and initiator concentrations is studied for these two types of stationary phases. The goal is to maximize their separation efficiency, thermal stability, and column lifetime, without sacrificing the unique selectivity of the stationary phase.

The following materials can be used to prepare cross-linked stationary phases comprising diionic liquid salts in accordance with the present invention: 1-vinylimidazole, 1-bromohexane, 1-bromononane, 1-bromododecane, 1,9-dibromononane, 1,12-dibromododecane, 1-bromo-6-chlorohexane, 1-methylimidazole, N-Lithiotrifluoromethanesulfonimide, AIBN, dichloromethane and ethyl acetate.

It has been demonstrated previously that room temperature ionic liquids act as broadly applicable, superb gas chromatographic stationary phases in that they exhibit a dual nature retention behavior. Consequently, ionic liquid stationary phases have been shown to separate, with high efficiency, both polar and nonpolar molecules on a single column. By producing stationary phases that are either partially or highly cross-linked, it is of interest to ensure that the solvation thermodynamics and solvation interactions inherent to ionic liquids are still retained by their immobilized analogues.

In another embodiment a mixed stationary phase (MSP) is provided. The MSP comprises at least one dicationic liquid salt of the invention and stationary phase material such as, but not limited to, polysiloxanes, polyethylene glycols ("PEGs"), methylpolysiloxanes, phenyl substituted methylpolysiloxane, nitrile substituted methylpolysiloxane and carbowax. Such MSPs can be used as a stationary phase in chromatography such as GC, LC and HPLC as well as in SPE and SPME. The MSPs can be non-cross-linked (e.g., absorbed or adsorbed on a solid support or column), can be "partially" cross-linked or "more highly" cross-linked (i.e., immobilized on a solid support or column). The dicationic liquid salt may also be cross-linked or otherwise reacted with the stationary phase material or merely mixed therewith.

Appropriate combinations of the dicationic liquid salt(s) and the stationary phase material(s) for producing a MSP is based on the particular application as are the proportions of the dicationic liquid salt(s) and the stationary phase material(s) in the MSP.

In a particular embodiment, the ratio of the dicationic liquid salt and the stationary phase material in the MSP is from about 1:9 (i.e., about 10% of dicationic liquid salt and 90% of stationary phase material) to about 9:1 (i.e., about 90% of dicationic liquid salt and about 10% of stationary phase material), about 1:3 (i.e., about 25% of dicationic liquid salt and about 75% of stationary phase material) to about 3:1 (i.e., about 75% of dicationic liquid salt and about 25% of stationary phase material), about 1:2 (i.e., about 33% of dicationic liquid salt and about 67% of stationary phase material) to about 2:1 (i.e., about 67% of dicationic liquid salt and about 33% of stationary phase material), or about 1:1 (i.e., about 50% of dicationic liquid salt and about 50% of stationary phase material) (w/w). Chromatography employing MSP may perform better, e.g., having higher selectivity, than chromatography employing dicationic liquid salt(s) or the stationary phase alone. As an example, an MSP comprising a simple mixture of about 67% (dibutyl imidazolium)$_2$(CH$_2$)$_9$ and about 33% of methylpolysiloxane with about 5% phenyl substitution was prepared and used to coat a column. This MSP was shown to exhibit better separation of an essential oil. A cross-linked version of the MSP can also be used.

In addition, the invention also provides methods of preparing MSPs, solid supports and/or columns containing same, the MSPs, solid supports, syringes, tubes, pipettes tips, needles, vials, and columns themselves, and the use of columns and solid supports containing such MSPs in chromatography and other analytical or separation techniques such as those described elsewhere herein.

F. OTHER SEPARATION AND ANALYTICAL TECHNIQUES

In a further embodiment, one or more dicationic liquid salts in accordance with the present invention can be used in analytical and separation technologies other than chromatography, all of which are considered as part of the present application. For example, dicationic liquid salts in accordance with the present invention can be used in, without limitation, SPE, SPME, TS-SPME, and certain types of mass spectrometry known as SPME/MALDI, as well as ion chromatography and ion exchange chromatography and headspace analysis.

In one other embodiment, there is provided a method of separating one chemical from a mixture of chemicals comprising the steps of providing a mixture of at least one first and at least one second chemical, exposing that mixture to at least one solid support including one or more dicationic liquid salts as described above using a device as described above and retaining at least a portion of the first chemical on the solid support for some period of time. "Retaining" in this context does not mean permanently. Separation can occur in a syringe device by removal of the device from the sample or ejection of the second chemical. In the case of a chromatography column, the first chemical will be absorbed or adsorbed at a different rate than the second chemical, which may be at a greater rate or a lower rate, thus resulting in separation. Both are moved through the column by a mobile phase, which can be a liquid or a gas and their interaction with the stationary phase (the ionic liquid materials on the solid support) at different rates causes separation. This is what is meant by "retention" in the context of chromatography. However, in certain types of chromatography, it is also possible that the first chemical is bound to the stationary phase while the second chemical is not and is carried through the column by the mobile phase until it elutes. The first chemical can be eluted or removed separately and this is also embraced by the word "retained."

In another embodiment, one or more DILSs can be used in SPE. In SPE, a sample contains an impurity or some other compound or analyte to be separated, identified and/or quantified. This sample can be placed into a container in which one or more DILS of the present invention can be present in, and more broadly, diionic liquid salts in an immobilized form. Ionic liquid materials can be bound (immobilized) to the walls of the container, adsorbed, or absorbed onto a bead or other structure so as to form a bead or other structure which may rest at the bottom of the container or be packed throughout the container much as a liquid chromatography column can be packed with stationary phase. Alternatively, the DILS can be immobilized by cross-linking or an analogous immobilization reaction as described herein on some sort of other solid support such as a bead, particles and/or other chromatographic media used in chromatography as described previously. These beads can also be placed at the bottom of, or can fill a container, much as is a packed column used for liquid chromatography. Of course, the solid support can be any structure placed anywhere within the container.

In a particular embodiment, the container is actually a syringe where the diionic liquid salt is affixed or disposed in one fashion or another at the base of the syringe, much as a filter. When the needle of the syringe is placed in a sample and the plunger is withdrawn, vacuum is formed drawing the sample up into the barrel of the syringe. This material would pass through at least one layer of diionic liquid salt, which would bind at least one of the components of the liquid. The sample liquid could then be spilled out or the plunger depressed to eject it, the latter forcing the sample back through the diionic liquid positioned at the bottom of the barrel.

The sample liquid can be analyzed either for the presence of certain materials or the absence of the material retained by the diionic liquid salt. Alternatively, the retained materials can be removed (such as by placing the materials in a different solvent) or not removed, and analyzed by other means. The same technique may be used in a preparative fashion and/or as a means of bulk purification as well.

In another embodiment, one or more DILSs may be used in SPME. In these techniques, a separation material (in this case an ionic liquid or in particular a diionic liquid salt in accordance with the present invention or ionic liquids mixed with adsorbents, particles and other chromatographic media) is absorbed, adsorbed or immobilized in one way or another on a fiber (e.g., polydimethylsiloxane/divinylbenzene (PDMS/DVB) fiber) or some other solid support which is applied to the plunger as a coating or as a sheet generally attached to a plunger in a microsyringe such as usually used in GC. A DILS of the invention can also be immobilized and attached directly without any separate solid support other than the plunger. This can be done using, for example, a film directly. The plunger is depressed, exposing the fiber and the fiber is then dipped into the sample of interest. The plunger can then be withdrawn to pull the fiber back into the barrel of the syringe, or at least the barrel of the needle for protection and transport. The syringe can then be injected through the septum of a gas chromatograph or some other device and the fiber thereby inserted into the column by redepressing the plunger of the microsyringe. The heat used in GC then volatilizes or otherwise drives the bound sample off where it is carried by the mobile phase through the GC column, allowing for separation and/or identification. It can also be eluted by a liquid mobile phase in an HPLC injector or unbuffered capillary electrophoresis. Immobilized DILS may also be used in conjunction with the coated stir bar technology, which is a higher capacity version of SPME. Some embodiments of this coated stir bar technology are sold under the trademark TWISTER™.

More specifically, SPME is a technique in which a small amount of extracting phase (in this case an ionic liquid and preferably a diionic liquid salt in accordance with the present invention) is disposed on a solid support, which is then exposed to a sample for a period of time. In situations where the sample is not stirred, a partitioning equilibrium between a sample matrix and the extraction phase is reached. In cases where convection is constant, a short time pre-equilibrium extraction is realized and the amount of analyte extracted is related to time. Quantification can then be performed based on the timed accumulation of analysis in the coating. These techniques are usually performed using open bed extraction concepts such as by using coated fibers (e.g., fused silica similar to that used in capillary GC or capillary electrophoresis, glass fibers, wires, metal or alloy fibers, beads, etc.), vessels, agitation mechanism discs and the like. However, in-tube approaches have also been demonstrated. In-tube approaches require the extracting phase to be coated on the inner wall of the capillary and the sample containing the analyte of interest is subject to the capillary and the analytes undergo partitioning to the extracting phase. Thus, material can be coated on the inner wall of a needle, for example, and the needle injected without the need for a separate solid support.

In addition, one or more DILSs can be immobilized by being bound or cross-linked to themselves and/or to a solid support as previously discussed in connection with manufacturing capillary GC columns. To do so, however, the species used should have at least one unsaturated group disposed to allow reaction resulting in immobilization.

Another type of SPME technique is known as task specific SPME or TS-SPME. TS-SPME allows for the separation or removal, and therefore the detection of particular species. These can include, for example, mercury and cadmium, although the technique is equally applicable to other materials. The concept is exactly the same as previously described with regard to SPME. However, in this instance, the diionic liquid salt(s) used are further modified such that they will specifically interact with a particular species. The first monocationic material can be coated, absorbed or adsorbed onto a fiber as previously discussed. A diionic liquid salt can also be absorbed or adsorbed in known fashion.

Finally, a particular sample can be suspended in a matrix that includes diionic liquid salts. This matrix can be loaded or immobilized on the fiber of an SPME syringe as described above and then injected into a mass spectrometer to practice a technique known as SPME/MALDI mass spectrometry. The matrix is exposed to a UV laser. This causes the volatilization or release of the sample much as heat does in a GC. This allows the sample to enter mass spectrometer where it can be analyzed.

G. DEVICES

The invention includes not only the use of DILSs, but also solid supports to which the DILSs are absorbed, adsorbed or immobilized as well as sampling devices such as, for example, pipettes, automatic pipettes, syringes, microsyringes and the like incorporating diionic liquid salts, which can be used in such analytical and separation techniques. Solid supports include, without limitation, mixed beds of particles coated with diionic liquid salts. These may be used as chromatographic media or for SPE, SPME, SPME/MALDI and ion exchange analysis. Particles may be composed of, for example, silica, carbons, composite particles, metal particles (zirconia, titania, etc.), as well as functionalized particles, etc. contained in, for example, tubes, pipettes tips, needles, vials, and other common containers.

Therefore, in one embodiment a device for chemical separation or analysis is provided. The device comprises a solid support and one or more dicationic liquid salts of the invention which is adsorbed, absorbed or immobilized on the solid support. In a particular embodiment, the device comprises a syringe, a hollow needle, a plunger, and the solid support being attached to the syringe.

Another embodiment is a device useful in chemical separation or analysis comprising: a solid support and one or more diionic liquid salts as described above adsorbed, absorbed or immobilized thereon. The device may be a column used in HPLC, GC or supercritical fluid chromatography (SFC) wherein the solid support is packed in a chromatographic column or wherein the solid support is a capillary column useful in GC.

The device may also be a syringe having a hollow needle defining an inner space, the needle being disposed at an end of a barrel and a plunger disposed within the barrel, the solid support being attached, mounted or affixed, irremovable or removably-attached, (collectively "attached") to the syringe such that it may be retracted into the inner space of the needle when the plunger is retracted from the barrel and exposed from within the needle when the plunger is inserted into the barrel. In one embodiment, the syringe is a microsyringe. In some embodiments, the one or more diionic liquid salts used in these devices also include monoionic materials which may be simply mixed therewith or which may be cross-linked to the diionic liquid salts of the invention. These may be absorbed, adsorbed or immobilized on the solid support. When immobilized, it is preferred that these ionic species include unsaturated groups.

EXAMPLES

The following examples are merely illustrative, and not limiting to this disclosure in any way.

Example 1

Synthesis of 1,3-propanediylbis[tripropylphosphonium]

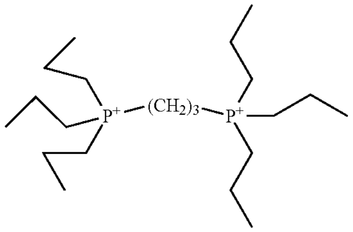

1,3-propanediylbis[tripropylphosphonium] was synthesized by dissolving one molar equivalent of 1,5-dibromopropane in isopropanol. To this solution, 3 molar equivalents of tripropylphosphine were added. The resulting mixture was stirred and heated to reflux for 48 hours. The solution was then cooled to room temperature and the solvent was removed by roto-evaporation. The crude product was then dissolved in deionized water and washed several times with ethyl acetate to remove any residual starting material. The water was then removed through roto-evaporation, followed by overnight drying in vacuum over phosphorous pentoxide.

Example 2

Synthesis of Dicationic Species

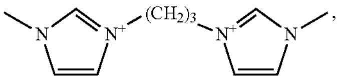,

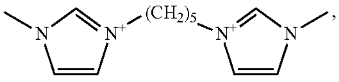,

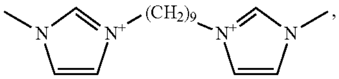,

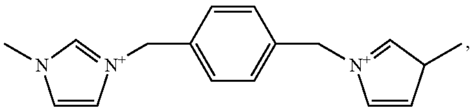,

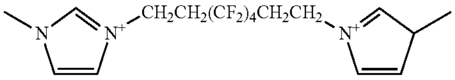,

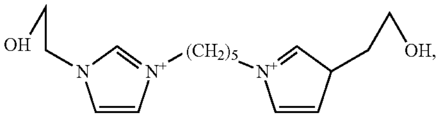,

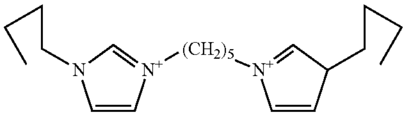 and

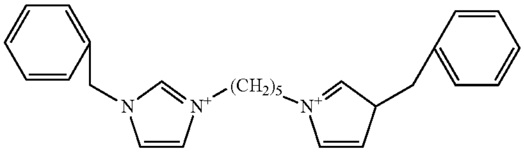

were made in an analogous manner as in Example 1.

Example 3

Synthesis of

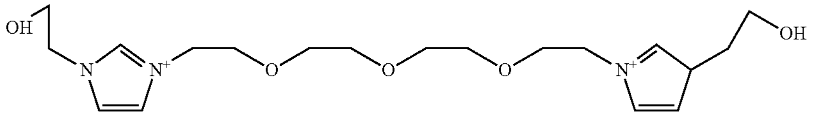 [SMILES: OCCC1C=C[N+](CCOCCOCCOCC[n+]2ccn(CCO)c2)=C1]

To produce this dicationic species, synthesis of the dibromopolyethylene glycol linker chain was first needed. This was accomplished by dissolving tetra(ethylene glycol) in ether, which was then cooled in an ice bath and reacted with 1.1 molar equivalents of phosphorous tribromide. The reaction was then refluxed for 2 hrs. Next the reaction mixture was poured over ice to react the excess $PBr_3$. The aqueous layer was discarded and the organic layer was washed four times with an aqueous sodium bicarbonate solution. The organic layer was then dried with sodium sulfate and filtered. Next, ether was removed by rotary evaporator and the resulting linker was placed under vacuum over night to ensure complete dryness. This linker was then reacted with the appropriate end groups to produce the dication.

Example 4

Use of Dicationic Species in ESI-MS for Anion Detection

All dicationic compounds were anion exchanged to their fluoride form to maximize complex formation between the dication and the injected analyte.

Methanol and water were of HPLC grade and obtained from Burdick and Jackson (Morristown, N.J.). Reagent grade sodium hydroxide and sodium fluoride were from Fisher Scientific. Anions used were purchased as either the sodium/potassium salt or as the free acid from Sigma-Aldrich (St. Louis, Mo.). Stock solutions of each anion were made weekly. Chemicals used for the syntheses of the dicationic compounds were also obtained from Sigma-Aldrich.

For direct injection analysis, a 40 μM dication-fluoride ($DF_2$) solution was directed into a Y-type mixing tee at 100 μL/min via a Shimadzu LC-6A pump. Also directed into the mixing tee was a carrier flow consisting of a 2:1 ratio of methanol to water at 300 μL/min from a Surveyor MS pump (Thermo Fischer Scientific, San Jose, Calif.). After the mixing tee, the final conditions were then 50/50 water/methanol with 10 μM $DF_2$ at a flow rate 400 μL/min. Sample introduction was done with the six port injection valve on the mass spectrometer using a 2 μL sample loop. A linear ion trap mass spectrometer (LXQ, Thermo Fisher Scientific, San Jose, Calif.) was used for this study. The ESI-MS settings were: spray voltage: 3 kV capillary temperature: 350° C., capillary voltage: 11 V, tube lens voltage: 105 V, sheath gas: 37 arbitrary units (AU), auxiliary gas: 6 AU. For the negative ion mode analysis, voltage polarities are reversed, while all other parameter settings were kept. ESI-MS settings for the optimized MCA detection are as follows: spray voltage: 4.5 kV, capillary temperature: 350° C., capillary voltage: 35 V, tube lens voltage: 80 V, sheath gas: 25 AU, auxiliary gas: 16 AU. The ion trap was operated using single ion monitoring (SIM).

For the chromatographic experiments, sample introduction was done by a Thermo Fisher Surveyor autosampler (10 μL injections). The stationary phase used was a 10 cm C-18 (3 μm particle size) obtained from Advanced Separations Technology (Whippany, N.J.). In the chromatograph of the multi-anion sample used for FIG. 1, the column was equilibrated with 100% water at 300 μL/min. At one minute, a linear gradient to 100% methanol began and was completed at three minutes. The addition of the $DF_2$ solution was done post-column at 100 μL/min via the mixing tee. To help with spray formation, the $DF_2$ was prepared as a methanol solution and again added post column. For the negative ion mode runs, pure methanol was introduced into the mixing tee as opposed to the $DF_2$ in methanol solution. The MS was again operated in SIM mode, monitoring the m/z values of each analyte for the entire run. Where single reaction monitoring was used, the normalized collision energy was set at 25 while the activation time was for 30 ms. Xcalibur and Tune Plus software was used for data collection and analysis.

It is recommended to further optimize when using a specific dication reagent for use in the detection of (a) specific anion(s). It is believed that these detection limits may be lowered when considerable time is given to optimization or when using a more sensitive mass spectrometer.

Results

The dicationic species tested are listed in Table 1 below.

| No. | Mass | Structure |
|---|---|---|
| VI | 206.3 | 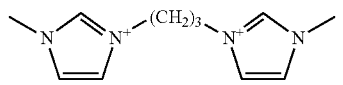 |
| VII | 234.3 | 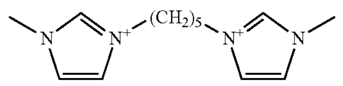 |
| VIII | 290.3 | 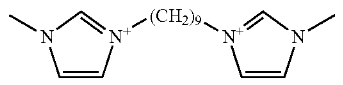 |
| IX | 268.3 | 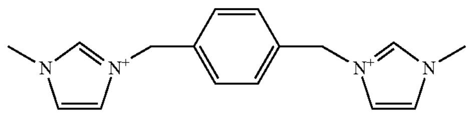 |

-continued

| No. | Mass | Structure |
|---|---|---|
| X | 420.4 | 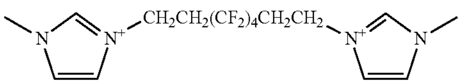 |
| XI | 384.4 | 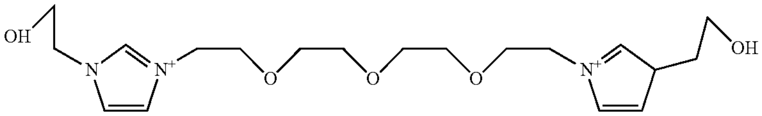 [SMILES: OCCC1C=C[N+](CCOCCOCCOCC[n+]2ccn(CCO)c2)=C1] |
| XII | 294.3 | 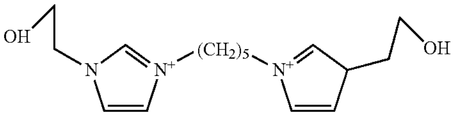 |
| XIII | 318.4 | 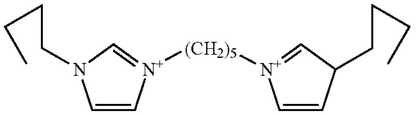 |
| XIV | 386.3 | 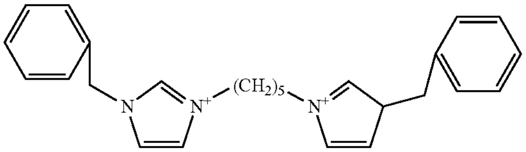 |

Table 2 lists the limits of detection (LOD) for each of the six representative anions (benzenesulfonate, cyanate, perfluorooctanic acid, iodide, nitrate, monochloroacetic acid) when successfully paired with the 9 different dicationic reagents. These values were determined by direct injection ESI-MS (see Experimental).

TABLE 2

| NCO LOD | | PFOA LOD | | $NO_3$ LOD | |
|---|---|---|---|---|---|
| Dication | Mass Inj (ng) | Dication | Mass Inj (ng) | Dication | Mass Inj (ng) |
| IX | 4.00E+00 | VIII | 1.22E−04 | VIII | 1.84E−03 |
| VIII | 6.42E+00 | XI | 5.00E−04 | VII | 6.00E−03 |
| X | 8.00E+00 | XIV | 4.50E−03 | XIII | 2.00E−02 |
| VI | 2.00E+01 | VII | 8.00E−03 | XIV | 2.00E−02 |
| VII | 2.00E+01 | X | 1.01E−02 | XII | 3.00E−02 |
| XIV | 1.50E+02 | VI | 1.40E−02 | IX | 4.00E−02 |
| XII | ND | IX | 1.41E−02 | X | 6.00E−02 |
| XIII | ND | XIII | 2.02E−02 | XI | 1.20E−01 |
| XI | ND | XII | 6.06E−02 | VI | 6.00E−01 |

| BZSN LOD | | MCA LOD | | I LOD | |
|---|---|---|---|---|---|
| Dication | Mass Inj (ng) | Dication | Mass Inj (ng) | Dication | Mass Inj (ng) |
| VIII | 2.06E−03 | XIV | 1.00E−02 | XIV | 4.00E−03 |
| X | 4.04E−03 | X | 1.24E−02 | VIII | 6.00E−03 |
| VII | 5.00E−03 | VIII | 1.50E−02 | VII | 8.00E−03 |
| XIII | 5.00E−03 | VII | 1.80E−02 | IX | 8.08E−03 |
| IX | 7.00E−03 | XIII | 2.00E−02 | VI | 1.00E−02 |
| VI | 8.00E−03 | IX | 3.00E−02 | XIII | 1.21E−02 |
| XII | 2.00E−02 | XI | 3.00E−01 | X | 2.00E−02 |
| XI | 5.00E−02 | XII | 5.00E−01 | XI | 2.00E−02 |
| | | VI | 2.00E+01 | XII | 3.04E−02 |

The use of dicationic reagents to detect singly charged anions via gas phase ion association has been shown to be a highly sensitive method and offers several significant improvements over using the negative ion mode when using traditional solvents. It was shown how this approach can be easily coupled to chromatography to study multiple anions. Also, the importance of choosing the correct dication species in order to get significant signals for the anions of interest is demonstrated.

What is claimed is:

1. A method of detecting at least one anion by ESI-MS, the method comprising:

adding to a sample at least one dicationic liquid salt comprising a dicationic species corresponding in structure to Formula I:

Formula I

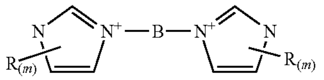

and at least one counter-anion, wherein the at least one counter-anion is $OH^-$;

wherein:

R is one or more substituents independently selected from the group consisting of alkyl, alkenyl, hydroxyl, alkoxy, carbocyclyl, carbocyclylalkyl, heterocyclyl, heterocyclylalkyl and hydroxyalkyl;

m is zero, 1, 2, 3 or 4;

B is a divalent fragment composed of a chain of one or more moieties selected from the group consisting of $C_1$-$C_{20}$-alkylene, $C_2$-$C_{20}$-alkenylene, $C_2$-$C_{20}$-alkynylene, $(—CH_2\text{-carbocyclyl-}CH_2—)_n$, $(—CH_2\text{-carbocyclyl-})_n$ and polysiloxyl;

wherein $C_1$-$C_{20}$-alkylene, $C_2$-$C_{20}$-alkenylene, and $C_2$-$C_{20}$-alkynylene optionally contain in the chain one or more heteroatoms selected from the group consisting of O, N, S and Si;

wherein B is optionally substituted with one or more substituents selected from the group consisting of alkyl, alkenyl, alkynyl, alkoxy and halo;

n is selected from the group consisting of 1 to 20, inclusive, to form a complex; and identifying the presence or non-presence of the complex formed between the at least one anion and the at least one dicationic liquid salt using ESI-MS.

2. The method of claim 1, wherein m is 1, 2, 3 or 4; and

B is $C_1$-$C_{20}$-alkylene, $C_2$-$C_{20}$-alkenylene, $(—CH_2\text{-carbocyclyl-}CH_2—)_n$ or $(—CH_2\text{-carbocyclyl-})_n$.

3. The method of claim 1, wherein there are at least two counter-anions independently selected from the group consisting of $F^-$ and $OH^-$;

m is 1, 2 or 3;

B is $C_1$-$C_{20}$-alkylene, $C_2$-$C_{20}$-alkenylene, $(—CH_2\text{-carbocyclyl-}CH_2—)_n$ or $(—CH_2\text{-carbocyclyl-})_n$; and n is 1 to 12, inclusive.

4. The method of claim 1, wherein there are at least two counter-anions independently selected from the group consisting of $F^-$ and $OH^-$;

R is $C_1$-$C_{10}$-alkyl, hydroxyl, carbocyclylalkyl, heterocyclylalkyl, hydroxyalkyl;

m is 1 or 2;

B is $C_1$-$C_{20}$-alkylene, $C_2$-$C_{20}$-alkenylene, $(—CH_2\text{-phenyl-}CH_2—)_n$ or $(—CH_2\text{-cyclohexane-}CH_2—)_n$, $(—CH_2\text{-phenyl-})_n$ or $(—CH_2\text{-cyclohexane-})_n$;

wherein B is optionally substituted with one or more substituents independently selected from the group consisting of F, Cl, Br, methyl, ethyl, propyl, butyl, methoxy, ethoxy, propoxy and butoxy;

wherein B optionally contains in the chain one or more oxygen atoms; and n is 1 to 12, inclusive.

5. The method of claim 1, wherein there are at least two counter-anions independently selected from the group consisting of $F^-$ and $OH^-$;

R is methyl, ethyl, propyl, butyl, hydroxyalkyl or benzyl;

m is 1;

B is $C_1$-$C_8$-alkylene or $(—CH_2\text{-phenyl-}CH_2—)_n$;

wherein B is optionally substituted with one or more substituents independently selected from the group consisting of F, Cl and Br;

wherein B optionally contains in the chain one or more oxygen atoms; and n is 1.

6. The method of claim 1, wherein the dicationic species is selected from the group consisting of:

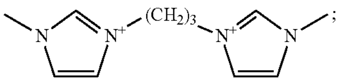
;

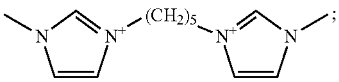
;

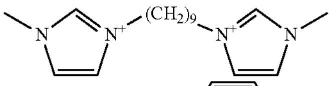
;

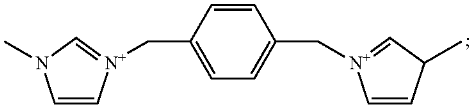
;

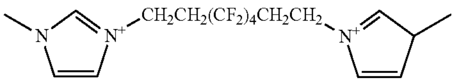
;

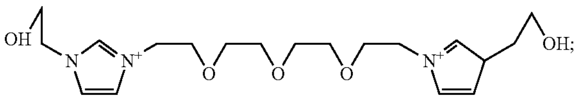
;

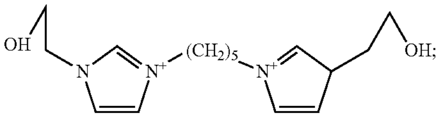
;

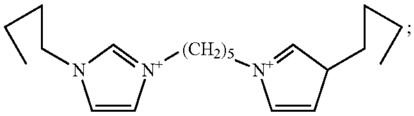
; and

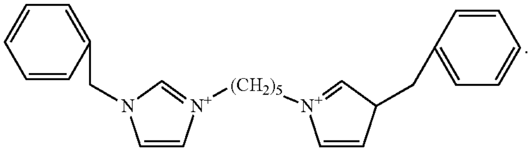
.

7. The method of claim 1, wherein ESI-MS is carried out in the positive ion mode.

8. The method of claim 1, wherein the dicationic liquid salt pairs with a single anion yielding a positively charged complex.

9. The method of claim 1, wherein the dicationic liquid salt is added to a carrier flow solvent.

10. The method of claim 9, wherein a dicationic liquid salt solution of about 1-μM to about 200 μM is added to the carrier flow solvent.

11. The method of claim 9, wherein the carrier flow solvent is a water-miscible organic solvent or a mixture of water and the water-miscible organic solvent.

12. The method of claim 11, wherein the water-miscible organic solvent is selected from the group consisting of methanol, ethanol, propanol, acetonitrile, tetrahydrofuran and dioxane.

13. The method of claim 1, further comprising coupling ESI-MS with a separation technique.

14. The method of claim 13, wherein the separation technique is selected from the group consisting of liquid chromatography, HPLC, ion chromatography, ion-exchange chromatography, SPE, SPME, TS-SPME and solid phase microextraction/MALDI.

15. The method of claim 13, wherein the dicationic liquid salt is added to the carrier flow solvent following the separation technique.

16. A stationary phase comprising at least one dicationic liquid salt comprising a dicationic species corresponding in structure to Formula I:

Formula I

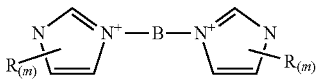

and at least one counter-anion;

wherein:

R is one or more substituents independently selected from the group consisting of $C_5$-$C_{20}$ alkyl, $C_3$-$C_{20}$ alkenyl, hydroxyl, alkoxy, carbocyclyl, carbocyclylalkyl, heterocyclyl, heterocyclylalkyl and hydroxyalkyl;

m is zero, 1, 2, 3 or 4;

B is a divalent fragment composed of a chain of one or more moieties selected from the group consisting of $C_1$-$C_{20}$-alkylene, $C_2$-$C_{20}$-alkenylene, $C_2$-$C_{20}$-alkynylene, (—$CH_2$-carbocyclyl-$CH_2$—)$_n$, (—$CH_2$-carbocyclyl-)$_n$ and polysiloxyl;

wherein $C_1$-$C_{20}$-alkylene, $C_2$-$C_{20}$-alkenylene, and $C_2$-$C_{20}$-alkynylene optionally contain in the chain one or more heteroatoms selected from the group consisting of O, N, S and Si;

wherein B is optionally substituted with one or more substituents selected from the group consisting of alkyl, alkenyl, alkynyl, alkoxy and halo;

n is selected from the group consisting of 1 to 20, inclusive.

17. The stationary phase of claim 16, wherein the at least one counter-anion is independently $F^-$ or $OH^-$;

m is 1, 2, 3 or 4; and

B is $C_1$-$C_{20}$-alkylene, $C_2$-$C_{20}$-alkenylene, (—$CH_2$-carbocyclyl-$CH_2$—)$_n$ or (—$CH_2$-carbocyclyl-)$_n$.

18. The stationary phase of claim 16, wherein there are at least two counter-anions independently selected from the group consisting of $F^-$ and $OH^-$;

m is 1, 2 or 3;

B is $C_1$-$C_{20}$-alkylene, $C_2$-$C_{20}$-alkenylene, (—$CH_2$-carbocyclyl-$CH_2$—)$_n$ or (—$CH_2$-carbocyclyl-)$_n$; and n is 1 to 12, inclusive.

19. The stationary phase of claim 16, wherein there are at least two counter-anions independently selected from the group consisting of $F^-$ and $OH^-$;

R is $C_5$-$C_{20}$-alkyl, hydroxyl, carbocyclylalkyl, heterocyclylalkyl, or hydroxyalkyl;

m is 1 or 2;

B is $C_1$-$C_{20}$-alkylene, $C_2$-$C_{20}$-alkenylene, (—$CH_2$-phenyl-$CH_2$—)$_n$ or (—$CH_2$-cyclohexane-$CH_2$—)$_n$, (—$CH_2$-phenyl-)$_n$ or (—$CH_2$-cyclohexane-)$_n$;

wherein B is optionally substituted with one or more substituents independently selected from the group consisting of F, Cl, Br, methyl, ethyl, propyl, butyl, methoxy, ethoxy, propoxy and butoxy;

wherein B optionally contains in the chain one or more oxygen atoms; and n is 1 to 12, inclusive.

20. The stationary phase of claim 16, wherein there are at least two counter-anions independently selected from the group consisting of $F^-$ and $OH^-$;

R is hydroxyalkyl or benzyl;

m is 1;

B is $C_1$-$C_8$-alkylene or (—$CH_2$-phenyl-$CH_2$—)$_n$;

wherein B is optionally substituted with one or more substituents independently selected from the group consisting of F, Cl and Br;

wherein B optionally contains in the chain one or more oxygen atoms; and n is 1.

21. The stationary phase of claim 16, wherein the dicationic species is selected from the group consisting of:

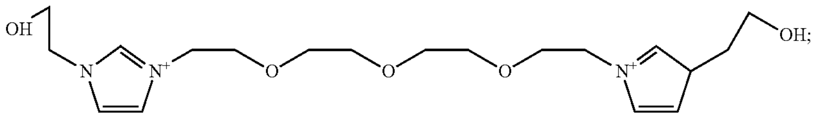

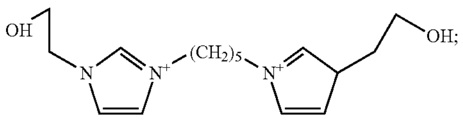

and

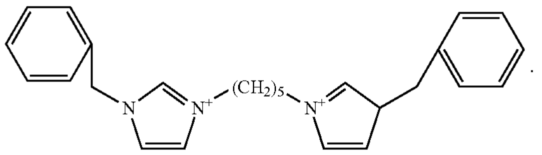

22. A mixed stationary phase comprising at least one dicationic liquid salt comprising a dicationic species corresponding in structure to Formula I:

Formula I

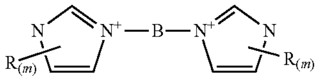

at least one stationary phase material, and at least one counter-anion;

wherein:

R is one or more substituents independently selected from the group consisting of $C_5$-$C_{20}$ alkyl, $C_3$-$C_{20}$ alkenyl, hydroxyl, alkoxy, carbocyclyl, carbocyclylalkyl, heterocyclyl, heterocyclylalkyl and hydroxyalkyl;

m is zero, 1, 2, 3 or 4;

B is a divalent fragment composed of a chain of one or more moieties selected from the group consisting of $C_1$-$C_{20}$-alkylene, $C_2$-$C_{20}$alkenylene, $C_2$-$C_{20}$-alkynylene, (—$CH_2$-carbocyclyl-$CH_2$—)$_n$, (—$CH_2$-carbocyclyl-)$_n$ and polysiloxyl;

wherein $C_1$-$C_{20}$-alkylene, $C_2$-$C_{20}$-alkenylene, and $C_2$-$C_{20}$-alkynylene optionally contain in the chain one or more heteroatoms selected from the group consisting of O, N, S and Si;

wherein B is optionally substituted with one or more substituents selected from the group consisting of alkyl, alkenyl, alkynyl, alkoxy and halo;

n is selected from the group consisting of 1 to 20, inclusive.

23. The mixed stationary phase of claim 22, wherein the at least one counter-anion is independently $F^-$ or $OH^-$;

m is 1, 2, 3 or 4; and

B is $C_1$-$C_{20}$-alkylene, $C_2$-$C_{20}$-alkenylene, (—$CH_2$-carbocyclyl-$CH_2$—)$_n$ or (—$CH_2$-carbocyclyl-)$_n$.

24. The mixed stationary phase of claim 22, wherein there are at least two counter-anions independently selected from the group consisting of $F^-$ and $OH^-$;

m is 1, 2 or 3;

B is $C_1$-$C_{20}$-alkylene, $C_2$-$C_{20}$-alkenylene, (—$CH_2$-carbocyclyl-$CH_2$—)$_n$ or (—$CH_2$-carbocyclyl-)$_n$; and n is 1 to 12, inclusive.

25. The mixed stationary phase of claim 22, wherein there are at least two counter-anions independently selected from the group consisting of $F^-$ and $OH^-$;

R is $C_5$-$C_{20}$-alkyl, hydroxyl, carbocyclylalkyl, heterocyclylalkyl, or hydroxyalkyl;

m is 1 or 2;

B is $C_1$-$C_{20}$-alkylene, $C_2$-$C_{20}$-alkenylene, (—$CH_2$-phenyl-$CH_2$—)$_n$ or (—$CH_2$-cyclohexane-$CH_2$—)$_n$, (—$CH_2$-phenyl-)$_n$ or (—$CH_2$-cyclohexane-)$_n$;

wherein B is optionally substituted with one or more substituents independently selected from the group consisting of F, Cl, Br, methyl, ethyl, propyl, butyl, methoxy, ethoxy, propoxy and butoxy;

wherein B optionally contains in the chain one or more oxygen atoms; and n is 1 to 12, inclusive.

26. The mixed stationary phase of claim 22, wherein there are at least two counter-anions independently selected from the group consisting of $F^-$ and $OH^-$;

R is hydroxyalkyl or benzyl;

m is 1;

B is $C_1$-$C_8$-alkylene or (—$CH_2$-phenyl-$CH_2$—)$_n$;

wherein B is optionally substituted with one or more substituents independently selected from the group consisting of F, Cl and Br;

wherein B optionally contains in the chain one or more oxygen atoms; and n is 1.

27. The mixed stationary phase of claim 22, wherein the dicationic species is selected from the group consisting of:

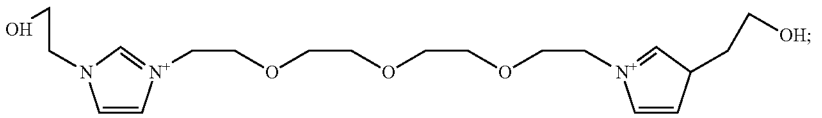

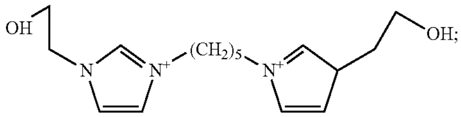

and

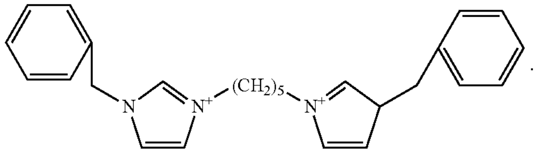

28. A method of detecting at least one anion by ESI-MS, the method comprising:

adding to a sample at least one dicationic liquid salt selected from the group consisting of:

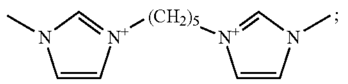

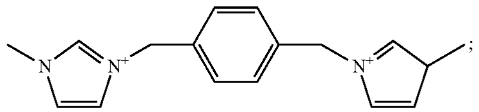

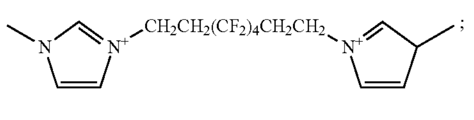

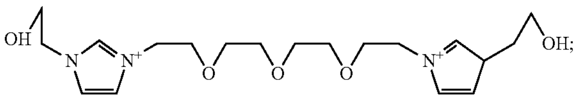

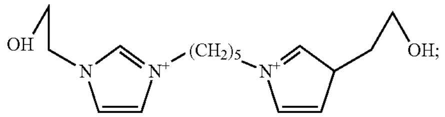

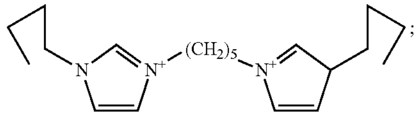

and

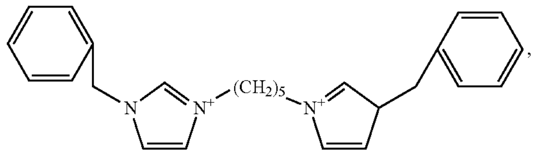

and at least one counter-anion, to form a complex; and identifying the presence or non-presence of the complex formed between the at least one anion and the at least one dicationic liquid salt using ESI-MS.

* * * * *